United States Patent [19]

Feld

[11] Patent Number: 4,605,757

[45] Date of Patent: Aug. 12, 1986

[54] METHOD OF PREPARING HALOGEN BENZOIC ACIDS FROM TOLUENES HALOGENATED IN THE NUCLEUS

[75] Inventor: Marcel Feld, Cologne, Fed. Rep. of Germany

[73] Assignee: Dynamit Nobel AG, Troisdorf, Fed. Rep. of Germany

[21] Appl. No.: 586,110

[22] Filed: Mar. 5, 1984

[30] Foreign Application Priority Data

Mar. 10, 1983 [DE] Fed. Rep. of Germany ....... 3308448

[51] Int. Cl.$^4$ ............................................ C07C 51/265
[52] U.S. Cl. ...................................... 562/416; 562/414
[58] Field of Search ................................. 562/416, 414

[56] References Cited

U.S. PATENT DOCUMENTS

| | | | |
|---|---|---|---|
| 3,012,038 | 12/1961 | O'Neill et al. | 562/416 |
| 3,679,740 | 7/1972 | Massie | 562/416 |
| 4,162,365 | 7/1979 | List et al. | 562/416 |
| 4,423,245 | 12/1983 | Lee | 562/416 |

FOREIGN PATENT DOCUMENTS 0227660 4/1958 Australia ............................ 562/416

OTHER PUBLICATIONS

Perry, Chemical Engineers' Handbook, 5th Ed., McGraw-Hill Book Co., New York, 1973, TP 155 P4.

*Primary Examiner*—Natalie Trousof
*Assistant Examiner*—Patricia M. Scott
*Attorney, Agent, or Firm*—Felfe & Lynch

[57] ABSTRACT

A method for the preparation of halogen benzoic acids by oxidation of the corresponding nuclear halogenated toluenes with oxygen or a gas containing oxygen, in acetic acid, with the addition of soluble cobalt and/or manganese compounds, and of sodium bromide, at elevated temperatures of about 80° to 220° C. and pressures of about 1 to 50 bar.

10 Claims, No Drawings

METHOD OF PREPARING HALOGEN BENZOIC ACIDS FROM TOLUENES HALOGENATED IN THE NUCLEUS

BACKGROUND OF THE INVENTION

The present invention relates to a method of preparing halogen benzoic acids by oxidation of the corresponding toluenes halogenated in the nucleus, especially by oxidation of o-chlorotoluene, p-chlorotoluene, 2,4-dichlorotoluene, p-fluorotoluene, o-bromotoluene, or p-bromotoluene, by means of oxygen or a gas containing oxygen, in acetic acid as solvent, in the presence of of soluble cobalt and/or manganese compounds and of a bromide ions supplying compound, at elevated temperatures of about 80° to 220° C. and pressures of about 1 to 50 bar, preferably 100° to 180° C. and 10 to 30 bar.

The toluenes halogenated in the nucleus, which are used as starting materials, can have one or more identical or different halogen atoms. The halogen benzoic acids obtained from them, such as for example o- or p-chlorobenzoic acid, can be used, for example, as starting products for the preparation of drugs, pest control agents and dyes. As products mono- and dichloro-benzoic acids and mono- and dibromo-benzoic acids are preferred.

The oxidation of toluenes halogenated in the nucleus by means of oxygen to form the corresponding halogen benzoic acids in the liquid phase is already described in the literature. In a kinetic research into the oxidation of chlorotoluenes (Zh. Prikl. Khim. (Leningrad) 1977, 50 (1), 133-6; Chem. Abstr. 87:22684 z), acetic acid is used as solvent, cobalt acetate as catalyst and sodium bromide as co-catalyst for the reaction, which is performed with pure oxygen. Technical problems, however, were ignored, such as for example corrosive action, or economic considerations in regard to product isolation. This also applies to the oxidation method described in EP-OS No. 0 002 749, which relates to the preparation of halogen benzoic acids among others, and which is characterized by the use of relatively small amounts of aliphatic carboxylic acids as solvents.

Less than 0.8 weight-parts of the solvent, acetic acid for example, per weight-part of the alkyl aromatics to be oxidized, is given as being advantageous. Higher solvent concentrations in the input mixture are said to be disadvantageous as regards transformation and selectivity of the oxidation. If larger amounts of solvent are used, the yield of aromatic carboxylic acid decreases, while on the other hand the content of the aromatic aldehyde formed as intermediate increases in the reaction mixture.

One disadvantage of greater amounts of solvent is seen in higher solvent losses, and also, due to the solubility of the target product, higher product losses and, in the case of distillative processing of the reaction mixture, a higher consumption of energy.

In the preparation of certain benzoic acids halogenated in the nucleus, such as for example o-chloro- or p-fluorobenzoic acid, the solvent concentration claimed in EP-OS No. 0 002 749 results in the fact that the entire reaction mixture stiffens upon cooling to a solid mass no longer capable of flowing. Consequently, consideration is also given to working up the reaction mixtures by distillation.

The distillation of the entire reaction mixture can lead to an end product of high purity, but it is relatively expensive technically and energy-wise when products are involved having melting points much above 100° C. It is especially difficult if the end products, such as o-chlorobenzoic acid or p-fluorobenzoic acid for example, are not at all distillable.

The difficulty involved in the distillation of the reaction mixture is worsened also by the great corrosiveness of a bromide ions containing carboxylic acid, which increases as the temperature increases and as the aqueous dilution decreases. This disadvantageous effect of the bromide co-catalyst, which is so advantageous to the reaction, calls for highly corrosion-resistant materials for all parts of the apparatus which come in contact with the reaction mixture at high temperatures.

The corrosion problem is aggravated in the case of the oxidation of toluenes halogenated in the nucleus also by the fact that halogen ions are formed by a partial oxidative destruction of starting, intermediate or end products. For example, in the oxidation of chlorotoluenes, chloride has been found in the mother liquor in addition to the bromide used as co-catalyst, after the separation of the end product. Even though this undesirable secondary reaction can be largely suppressed by suitable reaction conditions, halogen ions originating from the halogenated toluene can build up in the mother liquor if it is frequently reused.

It is the object of the present invention to develop a method of preparing benzoic acids halogenated in the nucleus, (nuclear halogenated) by oxidation of the corresponding nuclear halogenated toluenes with oxygen, while greatly reducing the corrosiveness of the reaction mixture and of the mother liquor, while enabling the target products to be recovered in a high yield and purity without the need to distill the entire reaction mixture, i.e., without distillation or sublimation of the target product. The isolation of the benzoic acid halogenated in the nucleus from the reaction should instead be performed by a conventional solid-from-liquid separation method.

THE INVENTION

This object is achieved in accordance with the invention by using, for each weight-part of halogenated toluene, 1.5 to 4.5 weight-parts of water-diluted acetic acid containing 1 to 35 weight-percent of water and an amount of a soluble ammonium and/or alkali and/or alkaline earth compound of more than 1.0 equivalent per equivalent of a compound supplying bromide ions used in the reaction mixture. Soluble cobalt and/or manganese compounds as acetates or compounds forming acetates in acetic acid are used as catalysts and bromides as sodium, ammonium, potassium bromides or hydrobromic acid are used as cocatalysts.

One feature of the method is the use of a water-diluted acetic acid containing 1 to about 35 weight-percent, preferably 5 to 25 weight-percent, of water as solvent, while for each weight part of the toluene halogenated in the nucleus, at least 1.5 weight-parts, preferably 2.0 to 3.5 weight-parts, of the solvent are used.

Another feature of the method is a content of ammonium and/or alkali and/or alkaline earth ions of 1.001 to 10 equivalents, preferably 1.01 to 8, most preferably 1.01 to 2.0 equivalents, which is already present in e.g. reused acetic acid solvent or which is added before the reaction, per equivalent of halogen ions in the reaction mixture. A consequence of the conditions in accordance with the invention, and at the same time a feature of a preferred method of procedure, is the frequent reuse of the mother liquor remaining after the separation of the target product and water of reaction, as a reaction medium for additional oxidations of the particular toluene halogenated in the nucleus.

To permit the intended isolation of the product by filtration, 1.5 to 4.5 weight-parts of solvent are used per weight-part of the halogenated toluene to be oxidized. The solvent in this case, of course, is not pure acetic acid, but a water-diluted acetic acid with a water content of 1 to 35 weight-percent, preferably 5 to 25 weight-percent, or the mother liquor recovered after separation of the target product and having the same water content.

The achievement of a high product yield is favored by the relatively high water content in the reaction mixture. In the case of products which are especially soluble in acetic acid, the product yield in the final separation can be further improved by adding additional water to the still hot reaction mixture, so as to establish in the reaction mixture an acetic acid-to-water ratio of 1:1 to 3:1, by weight.

In a preferred method of procedure, a high yield is obtained by the fact that, after the separation of the target product, the reaction water and the mother liquor obtained with the washing filtrates and amounts of acetic acid and water that might have been added to dilute the reaction mixture at the end of the reaction, the mother liquor is reused repeatedly as the reaction medium for additional oxidations of the halogenated toluene. In this manner, of course, not only are the product losses due to dissolution reduced overall, thus improving the yield, but at the same time the amount of catalyst required is considerably reduced, since the heavy metal catalyst is also reused with the mother liquor. Only the bromide losses incurred during the oxidation have to be compensated in the recycled mother liquor, and this is done preferably by adding appropriate amounts of hydrobromic acid.

The aim of high product purity is achieved in general simply by using water-diluted acetic acid to wash out the target product isolated from the cooled reaction mixture by one of the conventional methods of separating solids from liquids. Acetic acid having a water content, by weight, of 10 to 80%, preferably 30 to 60%, serves as the washing liquid in that case. The washing filtrate can be worked up by distilling it together with the mother liquor. Even without any additional purification operation, such as recrystallization or sublimation, o-chlorobenzoic acid, for example, can be obtained with a purity of better than 99.5%, even when the mother liquor is repeatedly recycled.

The aim of reducing the corrosive action of the reaction mixture and mother liquor is attained in the method of the invention by the degree of aqueous dilution of the solvent in the reaction mixture, combined with a larger content in gram-equivalents of ammonium and/or alkali and/or alkaline earth ions with respect to the bromide ion concentration. By this is meant not just the free or solvatized ions, but the sum of the ammonium, alkali or alkaline earth components present in the acetic acid medium upon the addition, for example, of the corresponding acetates or carbonates, independently of the degree of dissociation or the compounds which may be formed in said reaction mixture. The good corrosion-reducing action of a combination of water and ammonium, alkali or alkaline earth ions can be illustrated as follows. For example, the treatment of a strip of high-grade sheet steel, material No. 4571 weighing 15 grams and having a polished surface area of 42 sq.cm. (9.0×2.2×0.11 cm), with a solution of 4 g of cobalt bromide hexahydrate in 600 g of acetic acid containing 0.5% of water by weight, for 48 hours at 65° C., results in a loss of the tested material of 3.5 g (23.3% by weight, or 17.4 g per sq. m. per hour). When this test was repeated after adding 3.0 g of sodium acetate and raising the water content to one or more weight-percent, however, under the same experimental conditions, no weight loss was found within an accuracy of measurement of 1 mg. Such a remarkable positive effect was also achieved by the addition of ammonium, potassum or alkaline earth acetate or of substances yielding them in acetic acid solution, such as carbonates or hydroxides.

The bromide ion concentration considered necessary in the starting mixture for the method of the invention amounts to at least 0.0004 equivalents per mole of acetic acid. For the reduction of corrosiveness in accordance with the invention, the reaction mixture has, for each equivalent of bromine ions present and of halogen ions additionally formed during the performance of the process, 1.0 or more equivalents, and hence more than 0.0004 equivalents per mole of acetic acid, of the ammonium and/or alkali and/or alkaline earth component. In practice, a decided excess of the above-named cations, of 1.2 equivalents up to about 10 equivalents per equivalent of bromine ions, is placed in the starting mixture.

The concentration of the bromide preferentially used as co-catalyst in the method of the invention amounts to from 0.001 to 0.01 equivalents per mole of acetic acid. A portion of the bromide is lost in the course of the oxidation reaction. The bromine losses are compensated when the mother liquor is reused, by adding more bromide. For this purpose it is preferred to use hydrogen bromide in the form of its aqueous or acetic acid solution. Depending on the amount of bromide in the starting mixture, the preferred ammonium, alkali or alkaline earth concentration is about 0.002 to 0.04 equivalents per mole of acetic acid.

The advantages of the procedure in which the mother liquor is reused are especially apparent in the case of the preparation of o-chlorobenzoic acid, which is relatively easily soluble in acetic acid. According to Example 2, in the oxidation of o-chlorotoluene by the method of the invention, initially the yield of o-chlorobenzoic acid amounts to only about 80% of the theory. When the mother liquor was reused, a yield of better than 97% of the theory was realized. Thus, the total yield, after only one reuse of the mother liquor, increased to about 90% of the theory. After seven recyclings of the mother liquor, a total yield of o-chlorobenzoic acid was achieved, amounting, in accordance with Example 5, to 94.8% of the theory, while the product of the last of this series of tests, after conventional separation by filtering the target product out of the cooled reaction mixture and washing the filter cake with a water-diluted acetic acid, had a purity of 99.9%. A still more frequent reuse of the mother liquor, which would further improve the total yield, thus appears quite possible and practical.

The advantages of the method of the invention, however, do not relate merely to the technically simpler method of isolating the product, the reduction of the corrosion problems and the catalyst savings due to the possibility of reusing the mother liquor. Surprisingly, when the alkali concentration of the invention was used, it was found that the selectivity of the oxidation using greater amounts of solvent than those used in the above-cited state of the art, was greater. This becomes apparent upon a comparison of Example 6 with the initial test of the series of tests, described in Example 5, of the oxidation of o-chlorotoluene.

Example 5 and Example 6 are identical with regard to the amount of o-chlorotoluene, cobalt acetate, sodium bromide and sodium acetate put in. This is also true of the reaction and refinement conditions. The examples differ only in the amount and water content of the solvent during the reaction. The weight ratio of solvent to o-chlorotoluene in Example 6, which is 0.73:1, corresponds to the cited state of the art, while the related ratio in the input mixture of Example 5 performed under the conditions of the invention amounted to 2.45:1. After the oxidation had ended, the same solvent ratios as in Example 5 were established by the addition of acetic acid and water. After identical processing, a decidedly higher yield of o-chlorobenzoic acid resulted in Example 5, at 76.0% of the theory, than in Example 6 at 72.4% of the theory.

The advantages of aqueous dilution of the reaction mixture as regards yield will be evidenced by a comparison of Examples 2 and 3. In the case of Example 3, performed without water in the input mixture, the yield of o-chloro-benzoic acid, at 71.9% of the theory, was very unsatisfactory. Under otherwise the same reaction and product work-up conditions, Example 2, with 0.3 weight-parts of water per weight-part of acetic acid in the input mixture, resulted in a considerably higher yield of 80.7% of the theory.

The products made by the claimed process are useful intermediates. o-chlorobenzoic acid and o-bromobenzoic acid are raw materials for making saccharin (U.S. Pat. No. 4,145,349). p-chlorobenzoic acid is used to make e.g. Indomethacin (DE-OS No. 1.795.674). p-fluorobenzoic acid is a raw material for the production of antelmintics (DE-OS No. 2.029.637). 2,4-dichlorobenzoic acid may be converted into the diureticum furosemide according to U.S. Pat. No. 3,058,882.

EXAMPLES

EXAMPLE 1

In an autoclave of Hastelloy C, heated by circulating oil and provided with a stirrer, gas introduction tube, temperature sensor and condenser, 300 g of o-chlorotoluene, 660 g of acetic acid, 300 g of water, 15 g of cobalt acetate tetrahydrate, 5 g of sodium bromide and 5 g of sodium acetate were placed and heated under nitrogen at 150° C. At a temperature held in the range of 150° to 155° C., compressed air was then introduced. After the pressure had risen to 25 bar, the gas injection rate was regulated by the gas emergence rate of the exhaust gas expanded behind the condenser, which was set at 3 liters per minute. The exhaust gas was studied as regards amount and composition, especially its oxygen content, using appropriate measuring apparatus and analyzers. The reaction time was 210 minutes, the reaction time being reckoned from the beginning of the air injection to the end of the absorption of oxygen. The oxygen absorption was detected on the basis of the reduction of the oxygen content in the exhaust (<21%) below oxygen content of the injected compressed air. After the oxygen absorption had ended and the reaction mixture had cooled to room temperature, the crystallizate was isolated by filtration, washed with 450 g of a 50 wt-% acetic acid, and dried. The result was 291.7 g of o-chlorobenzoic acid (78.6% of the theory) having a purity of 99.9% as determined by gas chromatography.

EXAMPLE 2

The experiment described in Example 1 was repeated at the reaction temperature of 140° to 145° C., reducing the amount of input water to 200 g. 299.5 g of o-chlorobenzoic acid (80.7% of the theory) was obtained with a purity of 99.9%.

The mother liquor, combined with the washing filtrate, was concentrated by means of a fractionation column to 700 g of water-free solution. Bromide determination showed a bromide content of 0.038 mole. The resultant bromide loss of 22% of the amount put in, was compensated with 12 ml of a 7% solution of hydrobromic acid; 190 g of water and 300 g of o-chlorotoluene was added, and another oxidation was performed under the conditions set forth above. The result was 363.5 g of o-chlorobenzoic acid (97.9% of the theory with respect to freshly added o-chlorotoluene) with a purity of 99.9%.

EXAMPLE 3

(Example for comparison)

The experiment described in Example 1 was repeated without water in the input mixture. After a reaction time of 200 minutes at 140° to 145° C. and the conventional work-up, 193.7 g of o-chlorobenzoic acid was obtained (71.9% of the theory).

EXAMPLE 4

The experiment described in Example 1 was repeated with the input amounts reduced to 66 g of water and 6 g of cobalt acetate tetrahydrate, at a pressure of 10 bar and a reaction temperature of 150° C. 282.1 g of o-chlorobenzoic acid was obtained (76.0% of the theory).

EXAMPLE 5

The experiment described in Example 4 was repeated at a pressure of 25 bar, and 282.2 g of o-chlorobenzoic acid was obtained. As in Example 2, the mother liquor was concentrated to 700 g of water-free solution, the bromide losses (24.5% of the input) were compensated with 1.8 g of a 52% hydrobromic acid, 66 g of water and 300 g of o-chlorotoluene was added, and another oxidation was performed under the same reaction conditions. After conventional work-up, 368.7 g of o-chlorobenzoic acid was obtained (99.3% of the theory with respect to freshly added o-chlorotoluene), having a purity of 99.9%.

The mother liquor obtained after the second oxidation and combined with the washing filtrate was processed in the manner described and used for an oxidation under similar conditions. Then the same procedure was repeated another 5 times, and each time the mother liquor, dewatered and concentrated to 700 g, was combined with 66 g of water and 300 g of o-chlorotoluene plus the amount of hydrobromic acid required for compensation of the bromide losses, and was subjected to another oxidation reaction under always the same conditions.

In the eight tests in this series, a total of 2400 g of o-chlorotoluene was used and 2817 g of chlorobenzoic acid was isolated. The purity of the o-chlorobenzoic acid obtained in the 8th test amounted to 99.9%. In the mother liquor of the 8th test, 0.045 mole of chloride was still detected, in addition to 0.019 mole of bromide.

EXAMPLE 6

(Example for comparison)

The test described in Example 1 was repeated using 300 g of o-chlorotoluene, 6 g of cobalt acetate tetrahydrate, 5 g of sodium bromide, 5 g of sodium acetate, and only 210 g of acetic acid. After the absorption of oxygen ended, first 450 g of acetic acid and 66 g of water are added, before the work-up was performed in the manner described. The product was 276.4 g of o-chlorobenzoic acid (72.4% of the theory).

EXAMPLE 7

The first test of the series described in Example 5 was repeated, increasing the amount of sodium acetate to 15 g, and 280 g of o-chlorobenzoic acid was obtained (75.5% of the theory).

EXAMPLE 8 p-Chlorotoluene was oxidized to p-chlorobenzoic acid by the method explained in Example 1. The reaction mixture consisted of 250 g of p-chlorotoluene, 700 g of acetic acid, 50 g of water, 3.5 g of cobalt bromide hexahydrate, 3.5 g of cobalt acetate tetrahydrate and 11 g of a 50 wt-% solution of potassium hydroxide. The oxidation was performed at a pressure of 25 bar, a gas exhaust of 2.5 l/min, and a temperature of 150° to 170° C.; and yielded, after conventional work-up, 288 g of p-chlorobenzoic acid (90.5% of the theory) with a purity of 99.9%.

EXAMPLE 9

2,4-Dichlorotoluene was oxidized to 2,4-dichlorobenzoic acid by the method explained in Examples 2 and 5. The reaction mixture consisted of 300 g of 2,4-dichlorotoluene, 660 g of acetic acid, 73 g of water, 3 g of cobalt acetate tetrahydrate, 6 g of manganese acetate tetrahydrate, 5 g of ammonium bromide and 10 g of magnesium acetate. The oxidation was performed under the conditions described in Example 1, and after the conventional work-up yielded 303.5 g of 2,4-dichlorobenzoic acid of a purity of 98.5% (85.6% of the theory).

The mother liquor, concentrated as in Example 2 to 700 g of water-free solution, and having a bromide and chloride content of 0.25 and 0.09 wt-%, respectively, was treated with 5.1 g of 50% hydrobromic acid, 73 g of water and 300 g of dichlorotoluene, and subjected to another oxidation reaction under the same conditions, resulting in 337 g of 2,4-dichlorobenzoic acid (95.1% of the theory).

EXAMPLE 10

The test described in Example 1 was repeated using 300 g of p-fluorotoluene, 660 g of acetic acid, 132 g of water, 6 g of cobalt acetate tetrahydrate, 5 g of sodium bromide and 5 g of sodium acetate. In a reaction time of 240 minutes, after conventional work-up, 330.5 g of p-fluorobenzoic acid (86.6% of the theory) was obtained, with a purity of 99.9%.

As in Example 5, the mother liquor was reused another 3 times. Each time, 700 g of water-free mother liquor, after compensation of the bromide losses with hydrobromic acid, was used with 122 g of water and 300 g of p-fluorotoluene. In the 4 tests, a total of 1406.5 g of p-fluorobenzoic acid was obtained (92.1% of the theory).

EXAMPLE 11

The test described in Example 10 was repeated using 300 g of p-fluorotoluene, 660 g of acetic acid, 35 g of water, 2 g of cobalt acetate tetrahydrate, 4 g of manganese acetate tetrahydrate, 3 g of sodium bromide, and 5 g of sodium acetate. After oxygen absorption ended, the hot reaction mixture was diluted with 450 g of water and then worked up as usual. The result was 344.5 g of p-fluorobenzoic acid (90.3% of the theory) with a purity of 99.9%.

700 g of the water-free filtrate, processed by distillation, and having a bromide content of 0.28 wt-%, was subjected to another oxidation with 35 g of water, 0.7 g of a 50% hydrobromic acid, and 300 g of p-fluorotoluene, under the same conditions. The work-up was again performed after diluting the reaction mixture with 450 g of water, and yielded 363.5 g of p-fluorobenzoic acid (95.2% of the theory).

EXAMPLE 12

The test described in Example 1 was repeated using 300 g of p-bromotoluene, 700 g of acetic acid, 50 g of water, 6 g of cobalt acetate tetrahydrate, 5 g of sodium bromide and 5 g of sodium acetate. In a reaction time of 170 minutes, 292.4 g of p-bromobenzoic acid was obtained (80% of the theory).

EXAMPLE 13

The test described in Example 1 was repeated using 300 g of o-bromotoluene, 660 g of acetic acid, 60 g of water, 6 g of cobalt acetate tetrahydrate, 5 g of sodium bromide and 5 g of sodium acetate. After a reaction time of 155 minutes, 217 g of o-bromobenzoic acid was obtained (61.6% of the theory).

As in Example 5, the mother liquor, concentrated to 700 g of water-free solution, was used another 4 times for the oxidation, after the addition of 60 g of water and 300 g and 230 g, respectively, of o-bromotoluene. After the last test, performed with only 230 g of o-bromotoluene, the reaction mixture, still hot, was treated with 300 g of water before the conventional work-up. In all, 1430 g of o-bromotoluene was used in the 5 tests, and 1440 g of o-bromobenzoic acid (85.7% of the theory) was obtained.

It will be understood that the specification and examples are illustrative but not limitative of the present invention and that other embodiments within the spirit and scope of the invention will suggest themselves to those skilled in the art.

I claim:

1. A method for preparing a halogen benzoic acid comprising oxidizing the corresponding nuclear halogenated toluene with oxygen or a gas containing oxygen, in acetic acid as solvent, in the presence of soluble cobalt and/or manganese compounds present in catalytic amounts and of a bromide ions supplying substance selected from the group consisting of NaBr, NH$_4$Br, KBr, HBr, and CoBr$_2$, at elevated temperatures of about 80° to 220° C. and pressures of about 1 to 50 bars, wherein for each weight-part of halogenated toluene, 1.5 to 4.5 wt-parts of a water-diluted acetic acid are used, containing 1 to 35 wt-% of water and a content of a soluble ammonium and/or alkali and/or alkaline earth compound of more than 1.0 equivalents per equivalent of a bromide ion-yielding compound used in the reaction mixture.

2. The method of claim 1, wherein the nuclear halogenated toluene is p-chlorotoluene, o-bromotoluene, p-bromotoluene.

3. The method of claim 1, wherein the nuclear halogenated toluene is o-chlorotoluene or p-fluorotoluene.

4. The method of claim 1, wherein the nuclear halogenated toluene is 2,4-dichlorotoluene.

5. The method of claim 1, wherein for each equivalent of the bromide ion-yielding compound, 1.2 to 10 equivalents of a soluble ammonium, alkali and/or alkaline earth compound are used in the form of the acetates, hydroxides or oxides, carbonates or hydrogen carbonates.

6. The method of claim 2, wherein for each equivalent of the bromide ion-yielding compound, 1.2 to 10 equivalents of a soluble ammonium, alkali and/or alkaline earth compound are used in the form of the acetates, hydroxides or oxides, carbonates or hydrogen carbonates.

7. The method of claim 3, wherein for each equivalent of the bromide ion-yielding compound, 1.2 to 10 equivalents of a soluble ammonium, alkali and/or alkaline earth compound are used in the form of the acetates, hydroxides or oxides, carbonates or hydrogen carbonates.

8. The method of claim 4, wherein for each equivalent of the bromide ion-yielding compound, 1.2 to 10 equivalents of a soluble ammonium, alkali and/or alkaline earth compound are used in the form of the acetates, hydroxides or oxides, carbonates or hydrogen carbonates.

9. The method of claim 1, wherein the nuclear halogenated toluenes contain two halogens which are the same or different.

10. The method of claim 1 wherein the bromide concentration is 0.001 to 0.01 equivalents per mole of acetic acid.

* * * * *